United States Patent
Lee et al.

(10) Patent No.: US 12,178,388 B2
(45) Date of Patent: Dec. 31, 2024

(54) POWER PROVIDING DEVICE FOR MEDICAL DEVICE

(71) Applicant: MEDINTECH INC., Seoul (KR)

(72) Inventors: Chi Won Lee, Namyangju-si (KR); Myung Joon Kim, Gwacheon-si (KR); Suk Gyu Koh, Seoul (KR)

(73) Assignee: MEDINTECH INC., Seoul (KR)

( * ) Notice: Subject to any disclaimer, the term of this patent is extended or adjusted under 35 U.S.C. 154(b) by 0 days.

(21) Appl. No.: 18/288,180

(22) PCT Filed: Dec. 5, 2022

(86) PCT No.: PCT/KR2022/019637
§ 371 (c)(1),
(2) Date: Oct. 25, 2023

(87) PCT Pub. No.: WO2023/106772
PCT Pub. Date: Jun. 15, 2023

(65) Prior Publication Data
US 2024/0237879 A1    Jul. 18, 2024

(30) Foreign Application Priority Data

Dec. 8, 2021 (KR) .................. 10-2021-0174938

(51) Int. Cl.
*A61B 1/00* (2006.01)
*A61B 1/005* (2006.01)

(52) U.S. Cl.
CPC ...... *A61B 1/00029* (2013.01); *A61B 1/00128* (2013.01); *A61B 1/0057* (2013.01)

(58) Field of Classification Search
CPC ............ A61B 1/00029; A61B 1/00105; A61B 1/00128; A61B 1/0057
See application file for complete search history.

(56) References Cited

U.S. PATENT DOCUMENTS

| | | | |
|---|---|---|---|
| 2005/0137456 A1* | 6/2005 | Saadat | A61B 1/0055 600/114 |
| 2007/0093790 A1* | 4/2007 | Downey | A61B 17/2909 606/1 |
| 2014/0257333 A1* | 9/2014 | Blumenkranz | A61B 34/71 606/130 |
| 2015/0080658 A1 | 3/2015 | Chung et al. | |

FOREIGN PATENT DOCUMENTS

| | | |
|---|---|---|
| JP | 04-197235 A | 7/1992 |
| JP | 05-309066 A | 11/1993 |
| JP | 2002-325724 A | 11/2002 |
| KR | 10-2012-0014831 A | 2/2012 |
| KR | 10-2015-0030949 A | 3/2015 |

OTHER PUBLICATIONS

International Search Report for PCT/KR2022/019637 mailed Mar. 16, 2023 from Korean Intellectual Property Office.

* cited by examiner

*Primary Examiner* — Aaron B Fairchild
(74) *Attorney, Agent, or Firm* — Revolution IP, PLLC (57) ABSTRACT

The present invention relates to a power providing device for a medical device, the power providing device, including: a power source configured to generate power; a power transmission part configured to transmit power generated by the power source; a slider configured to operate by receiving power from the power transmission part and provide the same to a medical device; and a slider support supporting the slider and having a slider engagement portion operably engaging the slider.

7 Claims, 6 Drawing Sheets

POWER PROVIDING DEVICE FOR MEDICAL DEVICE

TECHNICAL FIELD

An aspect of the present disclosure relates to a power providing device for a medical device and, more particularly, to a power providing device internally provided with a power source for providing power to a medical device such that the medical device may operate.

BACKGROUND ART

The information disclosed in this section is only provided for an understanding of background information of embodiments of the present disclosure and should not be taken as a description of the prior art.

An endoscope generally refers to a medical instrument for examining the interior of the body for medical purposes. Such an endoscope may be referred to as a "bronchoscope," a "gastric endoscope," a "laparoscope," or a "colonoscope," depending on the area to be examined therewith. Unlike most other medical imaging devices, the endoscope is inserted directly into the body to capture images of internal organs, located inside the body.

Due to the development of optical fibers and the rapid development of optical technology and electronics, endoscope technology has reached the stage of the current electronic endoscope and has made a great contribution to the development of the field of gastroenterology. With the development of the electronic endoscope, the electronic endoscope is used not only in the diagnostic field to directly look into and perform histological examinations of a subject's body, but may also replace invasive surgery due to the rapid development of various treatment endoscopes.

The configuration of the endoscope may generally include an insertion tube configured to be inserted into the patient's body with a bendable section and a flexible portion, a control body connected to one end of the insertion tube to control the bending motion of the bendable section, a connector coupled to a light source, or the like, and a universal code separating the control body and the connector.

The endoscope has a structure in which a mechanical cord (or cable) is disposed between the bendable section and the control body to control the bending motion of the bendable section, and the mechanical cord is connected to a control knob disposed on the control body. According to the structure of the endoscope, when the user, i.e., a doctor, manually operates the control knob, the mechanical cord transmits power to perform the bending motion of the bendable section.

An endoscopic system may include an endoscope, a light source, and an image processing device. A generally known conventional endoscopic system includes a light source device emitting light to view organs inside the body, an image sensor receiving light signals of the light input from the light source device and reflected from the surface of the organs inside the body and converts the light signals into electrical signals (image signals), and a camera including a camera chip including an encoder converting the image signals into electronic signals for observation through a monitor, the camera being provided at a leading edge of the endoscope.

In the meantime, while a doctor is performing an endoscoy, an emergency situation may occur that could be fatal to a patient. However, endoscopes with a conventional structure require the doctor to manually control the bending motion of a bendable section by manually operating a knob in such an emergency situation, which may be problematic because the doctor may only be able to focus on operating the knob, making it difficult to overcome the tense situation, and the bending motion of the bendable section may not be performed accurately.

Therefore, endoscopes that may perform the bending motion of the bendable section by automatic operation of a power source rather than manual operation by a doctor have been developed. However, the problem with these endoscopes is the way the endoscope is powered. In this regard, research is underway into a system that enables the endoscope to receive not only light but also power from a light source device.

In order to provide power to the endoscope, a method may be applied in which an external device receives a control signal to control power and outputs power corresponding to the control signal. In this case, it is urgently necessary to develop a power transmission system that may transmit an accurate amount of power to the endoscope so that the movement of the endoscope may accurately follow the control signal when a control signal is received, for example.

The information disclosed in the Background section is technical information that the inventors possessed for, or acquired during, derivation of embodiments of the present disclosure and should not be taken as known technology disclosed to the public before the filing of the embodiments of the present disclosure.

DISCLOSURE

Technical Problem

Accordingly, an aspect of the present disclosure has been made in consideration of the above-described problems occurring in the related art, and the present disclosure provides a power providing device for a medical device, the power providing device having a novel structured power source capable of outputting an accurate amount of power in response to the received control signal.

The objectives of the present disclosure are not limited to the aforementioned descriptions, and other objectives not explicitly disclosed herein will be clearly understood by a person having ordinary knowledge in the art from the description provided hereinafter.

Technical Solution

According to an aspect of the present disclosure, a power providing device for a medical device may include one or more among: a power source configured to generate power; a power transmission part configured to transmit power generated by the power source; a slider configured to operate by receiving power from the power transmission part to provide the same to a medical device; and a slider support supporting the slider and having a slider engagement portion operably engaging the slider.

In some embodiments, the slider engagement portion may include a rail engagement structure formed on the slider support and the slider to allow the slider to move linearly along the slider support.

In some embodiments, the medical device may have a first engagement portion configured to receive power, and the slider may have a second engagement portion configured to interact with the first engagement portion to provide power to the first engagement portion.

In some embodiments, the first engagement portion may have a first protrusion or a first recess, and the second engagement portion may have a second recess, corresponding to the first protrusion, or a second protrusion, corresponding to the first recess.

In some embodiments, the medical device may include an endoscope, and the first engagement portion may be disposed on a connector of the endoscope.

In some embodiments, the power transmission part may include a pinion gear connected to a driving shaft of the power source, and a rack gear formed on one side of the slider and engaged with the pinion gear.

In some embodiments, the slider support may be provided with a slider receptacle formed to surround, receive, and engage with the slider with a rail structure.

In some embodiments, the slider may provide power to the medical device by performing a vertical linear motion.

In some embodiments, the medical device may include a bendable section inserted into the subject's body to perform a bending motion in order to collect image information of the interior of the subject's body.

Here, the motion of the slider may have a range corresponding to a range of bending angles of the bendable section.

In some embodiments, the power providing device may include: a control command receiver, receiving a control command signal controlling a travel distance of the slider from the medical device; and a power source controller configured to control power generation of the power source on the basis of the control command signal received by the control command receiver.

Advantageous Effects

According to an embodiment of the present disclosure described hereinbefore, provided is a power providing device having a novel structure capable of outputting an accurate amount of power in response to the received control signal.

In addition, the present disclosure has a variety of effects with excellent versatility depending on the embodiment, and such effects may be clearly understood from the following description of embodiments.

DESCRIPTION OF DRAWINGS

The following drawings accompanying the specification illustrate embodiments of the present disclosure and, together with the foregoing disclosure, serve to provide further understanding of the technical spirit of the present disclosure, and thus, the present disclosure should not be construed as being limited to the drawings, wherein.

MODE FOR INVENTION

Advantages and features of the present disclosure, as well as methods of realizing the same, will be more clearly understood from the following detailed description of embodiments when taken in conjunction with the accompanying drawings. However, the present disclosure is not limited to specific embodiments to be described hereinafter but should be understood as including a variety of modifications, equivalents, and alternatives within the spirit and scope of the present disclosure. Rather, these embodiments are provided so that the description of the present disclosure will be complete and will fully convey the scope of the present disclosure to a person having ordinary skill in the art in the technical field to which the present disclosure pertains. In the following description of the present disclosure, a detailed description of related known technology will be omitted when the description may render the subject matter of the present disclosure unclear.

The terminology used in this application is used to describe specific embodiments only and is not intended to limit the invention. Expressions in the singular include the plural unless the context clearly indicates otherwise.

In the present application, the terms "includes" or "has" and the like are intended to designate the presence of the features, numbers, steps, actions, components, parts, or combinations thereof described in the specification, and are not intended to preclude the possibility of the presence or addition of one or more other features, numbers, steps, actions, components, parts, or combinations thereof. Terms such as first, second, and the like may be used to describe various components, but the components are not to be limited by such terms. Such terms are used only to distinguish one component from others.

Hereinafter, embodiments according to the present disclosure will be described in detail with reference to the accompanying drawings, wherein identical or corresponding components are denoted by the same reference numerals and duplicate descriptions thereof are omitted.

Figure 1:
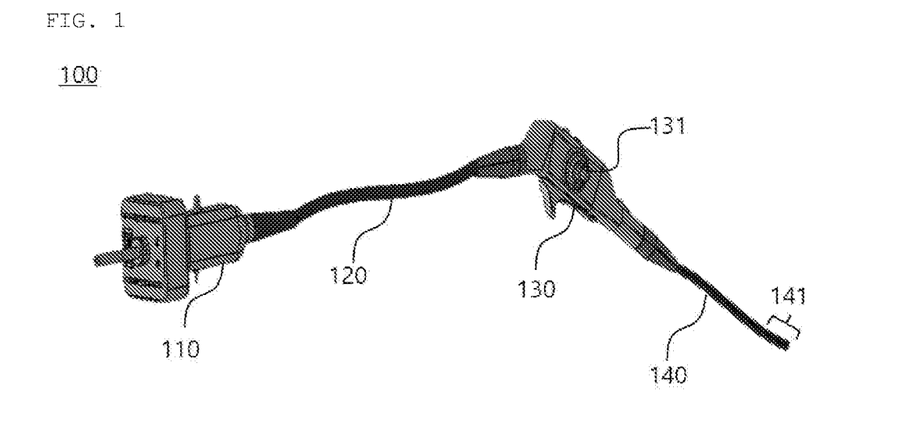
FIG. 1 illustrates an endoscope according to an embodiment of the present disclosure.

FIG. 1 illustrates an endoscope according to an embodiment of the present disclosure.

Figure 2:
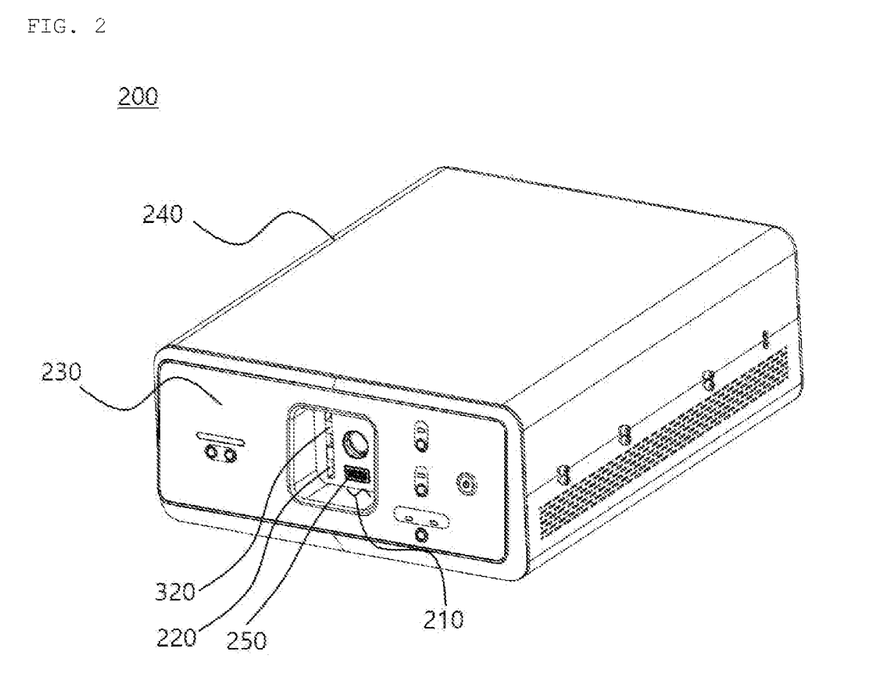
FIG. 2 illustrates a power providing device according to an embodiment of the present disclosure.

FIG. 2 illustrates a power providing device according to an embodiment of the present disclosure.

The power providing device 200 according to an embodiment of the present disclosure may include a device performing a function of providing power to a medical device.

As used herein, a medical device may include an endoscope 100. The endoscope 100 may include an instrument that may be inserted into the patient's body to diagnose, treat, mitigate, cure, prevent a disease, or the like, while collecting imaging information.

In some embodiments, the endoscope 100 may include one or more among an insertion tube 140, a control body 130, a universal cord 120, and a connector 110.

In some embodiments, the control body 130 may be disposed between one end of the insertion tube 140 and one end of the universal cord 120, and the connector 110 may be connected to the other end of the universal cord 120.

The insertion tube 140 may be a portion that is inserted into the patient's body when a user, i.e., a doctor, performs an endoscopy on the patient using the endoscope 100. The insertion tube 140 may include a tube tip, a bendable section 141, and a flexible portion.

The tube tip may be configured to illuminate a target area, collect image information, perform a treatment, or the like. The tube tip may be disposed at the end of the insertion tube, and may include an illumination means for illuminating the interior of the subject's body, an imaging means for imaging the interior of the subject's body, a biopsy channel for collecting tissue from the interior of the subject's body, an air-water channel for spraying air, water, or the like for various purposes, and the like.

The bendable section 141 performs a bending motion by the user's operation, and may be bent and may travel along the interior of the curved tubular organ inside the body. The tube tip may be disposed at an end of the bendable section 141, and the bendable section 141 may bend at the end in the bending motion to position the tube tip in a direction desired by the user.

The flexible portion may be disposed between the bendable section 141 and the control body 130, and may be a portion that moves along with the bendable section 141 when the bendable section 141 travels through the gastrointestinal tract inside the patient's body.

The control body 130 may be equipped with a controller 131 to control the bending motion of the bendable section 141, and may be provided with a flow control valve or flow control switch to control a flow of air or water, or suction. The controller 131 may include, for example, a joystick.

The insertion tube 140 may be connected to one side of the control body 130, and the universal cord 120 may be connected to the other side. The end of the universal cord 120 may be connected to the connector 110.

The connector 110 may function to connect the endoscope 100 to an external device. Here, the external device may include a power providing device 200. The power providing device 200 may include, for example, a light source, an image processing device, and the like.

When the endoscope 100 is connected to the light source or the image processing device via the connector 110, the endoscope 100 may receive light from the light source via the connector 110 and illuminate the interior of the patient's body, and the image information about the interior of the patient's body collected by the endoscope 100 may be transmitted to the image processing device via the connector 110.

The universal cord 120 connects the control body 130 and the connector 110, and may serve to separate the connector 110 and the control body 130 so that a user may hold the control body 130 and move it easily when using the endoscope 100. In some embodiments, the universal cord 120 may be omitted and the connector 110 may be connected to the other side of the control body 130.

Figure 3:
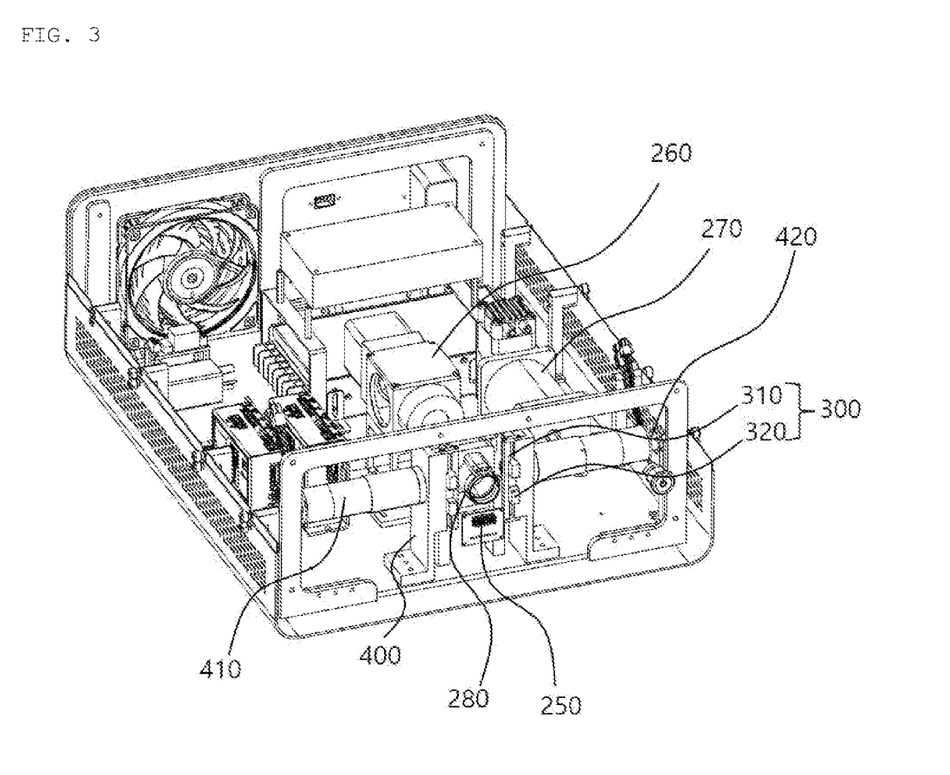
FIG. 3 illustrates an upper housing portion removed from the power providing device of FIG. 2.
Figure 4:
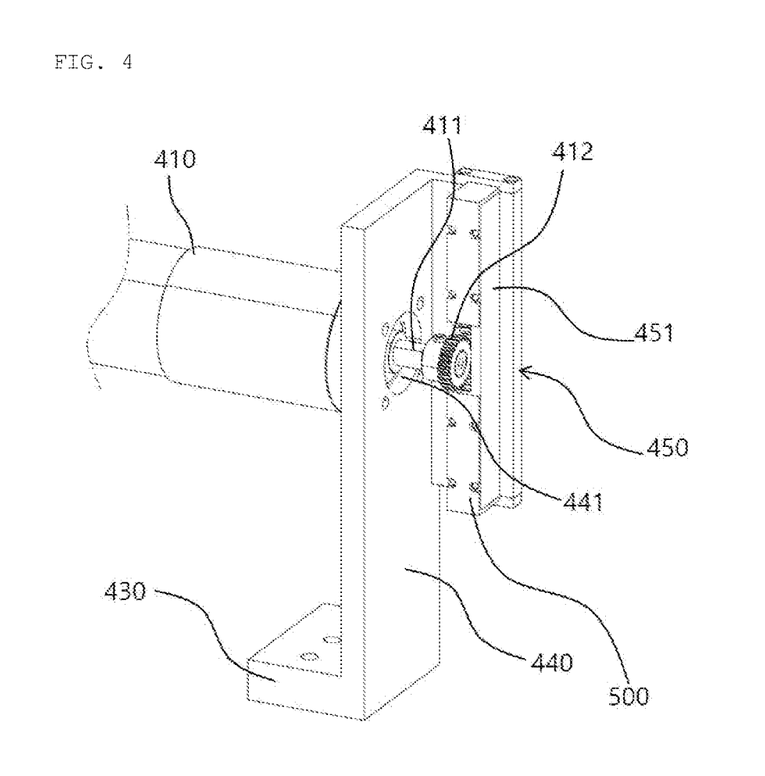
FIG. 4 illustrates a slider support according to an embodiment of the present disclosure.

FIG. 3 illustrates the power providing device with an upper housing portion removed therefrom in the state illustrated in FIG. 2, and FIG. 4 illustrates a slider support according to an embodiment of the present disclosure.

Figure 5:
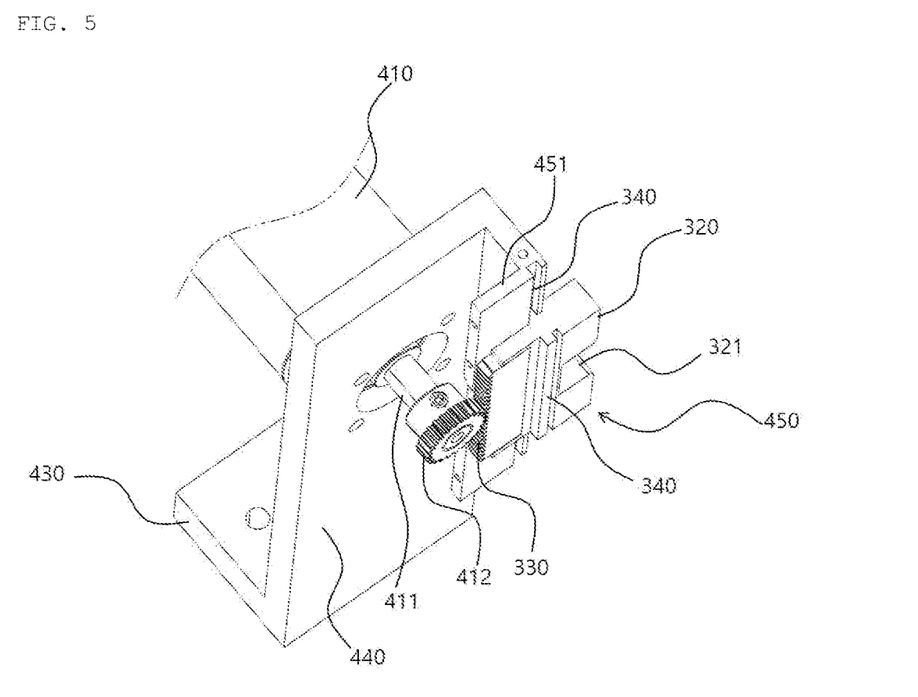
FIG. 5 is a top view illustrating the slider support of FIG. 4.
Figure 6:
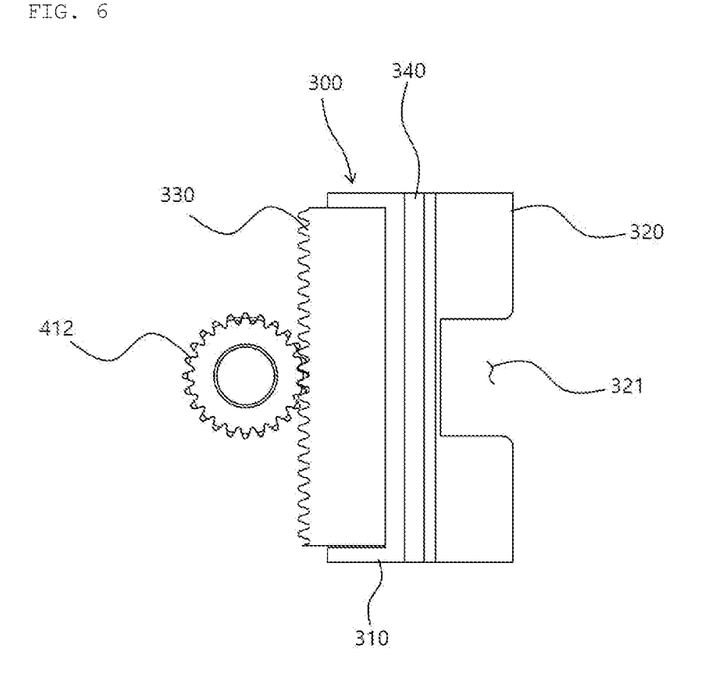
FIG. 6 illustrates a slider according to an embodiment of the present disclosure.

FIG. 5 is a top view illustrating the slider support of FIG. 4, and FIG. 6 illustrates a slider according to an embodiment of the present disclosure.

Figure 7:
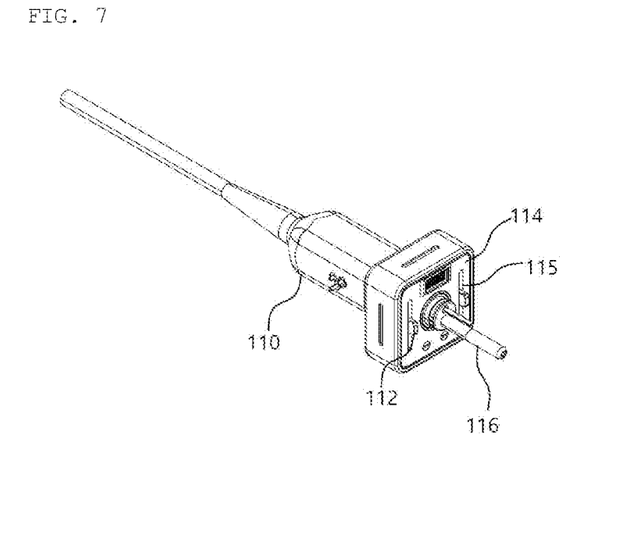
FIG. 7 illustrates a connector of an endoscope according to an embodiment of the present disclosure.
Figure 8:
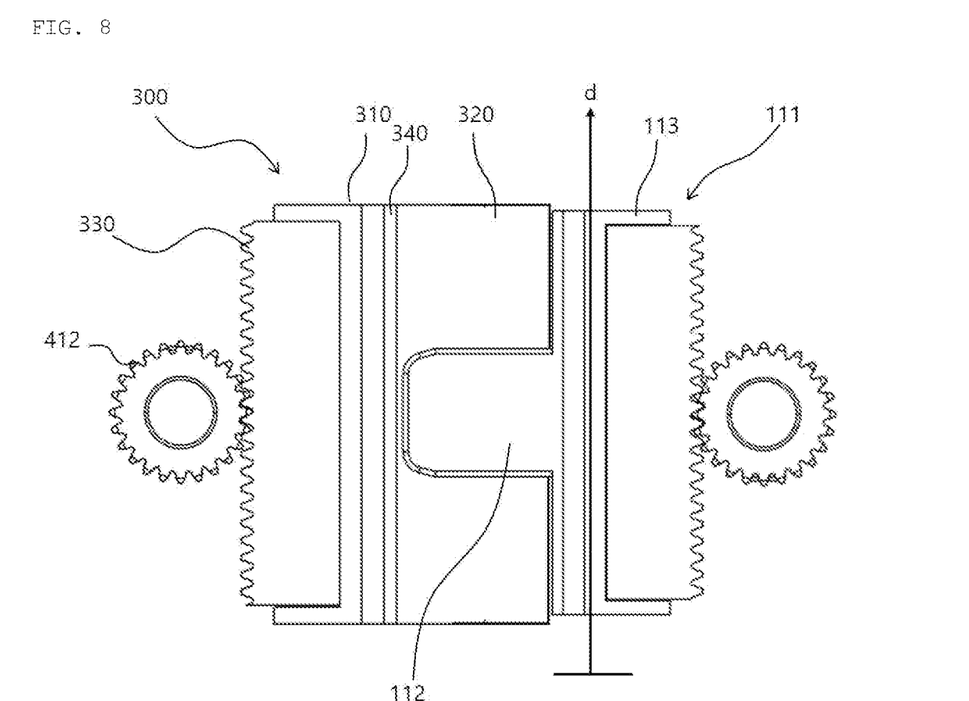
FIG. 8 illustrates the state of first and second engagement portions being engaged with each other according to an embodiment of the present disclosure.

FIG. 7 illustrates a connector of the endoscope according to an embodiment of the present disclosure, and FIG. 8 illustrates first and engagement portions engaged with each other according to an embodiment of the present disclosure.

In some embodiments, a power providing device 200 may include one or more among: a power source 410 generating power; a power transmission portion 330, transmitting power generated by the power source 410; a slider 300 operating with the power from the power transmission portion 330, 412 to provide power to a medical device; and a slider support 400 that supports the slider 300 and has a slider engagement portion 340 to which the slider 300 is operably coupled.

The power source 410 may include a power generating device. The power source 410 may include, for example, a motor. The power transmission portion 330, 412 may serve to transmit power generated by the power source 410 to the slider 300. The slider 300 may receive power from the power transmission portion 330, 412 and slide to provide power to the medical device.

The slider support 400 may function to support the slider 300 so that the slider 300 may move along the slider support. The slider 300 and the slider support 400 may be engaged with each other via the slider engagement portion 340.

The slider engagement portion 340 may include a concavo-convex structure formed in the slider support 400 and the slider 300 according to embodiments. The concavo-convex structure may have a structure extending in a vertical direction. The slider 300 and the slider support 400 are engaged with each other by the concavo-convex structure, and the slider 300 may be moved linearly up and down on the slider support 400 via the concavo-convex structure.

Hereinafter, the power providing device 200 will be described in detail.

A control panel 230 may be disposed on the front of the housing 240 of the power providing device 200. A user may operate the control panel 230 to drive the power providing device 200.

The control panel 230 may be disposed on a front portion of the power providing device 200, and a connector receptacle 210 may be disposed in a center portion of the control panel 230 so that the connector 110 of the endoscope 100 is connected thereto. On an inner side of the front portion of the power providing device 200, the slider support 400 may be disposed.

The power providing device support 400 may comprise a body portion 440 formed vertically to support the power source 410, and a bottom fastener 430 and a slider receptacle 450, configured to fasten the body portion 440 to the bottom.

The bottom fastener 430 may be formed by a bend in the lower end of the body portion 440, according to embodiments. The body portion 440 and the slider receptacle 450 may be formed perpendicularly to each other, i.e., a first plate of the slider support 400 constituting the body portion 440 and a second plate on which the slider receptacle 450 is formed may be disposed perpendicularly to each other.

The slider receptacle 450 may be formed to entirely surround the slider 300, according to embodiments. The slider 300 may include a body portion 310 and a second engagement portion 320. A rail structure may be formed on both sides of the body portion 310 of the slider 300. The rail structure may include a concavo-convex shape according to embodiments.

The slider receptacle 450 may have two rail sidewalls 451 facing and surrounding the two sides of the body portion 310 of the slider 300. Additionally, a lid cover 500 covering a rear surface of the body portion 310 may be disposed closing the rear surface of the two rail sidewalls 451. The body portion 310 may be surrounded on three sides by the two rail sidewalls 451 and the lid cover 500. The inner surfaces of the two rail sidewalls 451 may be provided with a rail structure formed thereon. The rail structure of the slider receptacle 450 may be formed to correspond to the shape of the rail structure formed on the body portion 310 of the slider 300. Such a structure allows the slider 300 to slide smoothly within the slider receptacle 450.

A through-groove may be formed in the front portion of the slider receptacle 450. The through-groove is a structure elongated in a vertical direction.

While the body portion 310 of the slider 300 is accommodated in the slider receptacle 450, the second engagement portion 320 of the slider 300 may pass through the through-groove and be exposed externally. A connector receptacle 210 may be formed on the front side of the slider receptacle 450, a through-slot 220 may be formed on an inner surface of the connector receptacle 210, and the second engagement portion 320 may pass through the through-slot 220 and be exposed externally on the inner surface of the connector receptacle 210.

The power source 410 may be disposed and attached to the slider support 400. At the opposite end of the portion of the power source 410 that is attached to the slider support 400, a location information collecting part 420 may be disposed to collect location information such as a rotation speed, a rotation amount, etc., of a driving shaft 411 of the power source 410. The location information collecting part 420 may include, for example, an encoder.

In the body portion 440 where the power source 410 is disposed, a driving shaft through-hole 441 may be formed so that the driving shaft 411 is output from the power source 410 may be disposed therethrough. A pinion gear 412 may be disposed at an end of the driving shaft 411 exposed through the driving shaft through-hole 441.

The slider receptacle 450 may have an overall shape of a hexahedron. The receptacle may include two rail sidewalls 451, a top sidewall, a bottom sidewall, and a rear sidewall that hold the body portion 310 of the slider 300 on both sides so that the body portion 310 may be slidably moved. A through-hole may be formed in a center portion of the rear sidewall, and the body portion 310 of the slider 300 may be exposed through the through-hole.

A rear surface of the body portion 310 may be toothed, i.e., a rack gear 330 may be formed. The driving shaft 411 that is output from the power source 410, the pinion gear 412 connected to the end of the driving shaft 411, and the rack gear 330 of the body portion 310 may constitute the power transmission portion 330, 412.

By such a structure, power may be transmitted from the pinion gear 412 to the rack gear 330 by engagement between the rack gear 330 formed at the rear of the body portion 310 and the pinion gear 412 disposed at the end of the driving shaft 411 of the power source 410. That is, when the driving shaft 411 of the power source 410 rotates, the pinion gear 412 rotates to cause the rack gear 330 to move up and down so that the body portion 310 of the slider 300 move up and down, and thus the secondary engagement portion 320 integrally formed with the body portion 310 moves up and down.

In some embodiments, the connector 110 of the endoscope 100 includes a power receiving part 111 to receive power transmitted from an external source. The power receiving part 111 may function as a slider 300. Inside the connector 110 is a mainframe, and a power receiving part receptacle may be disposed on the front of the mainframe. The power receiving part 111 may be slidably movably connected within the power receiving part receptacle. An inner surface of the power receiving part receptacle and both sides of the power receiving part 111 are respectively formed with rail structures, the shapes of which correspond to each other. This structure allows the power receiving part 111 to slide along the rail structure inside the power receiving part.

The power receiving part 111 may include a first engagement portion 112 and a base portion 113 from which the first engagement portion 112 extends. On either side of the base portion 113, a rail structure is formed to correspond to the shape of and to engage with the rail structure formed on the inner side of the power receiving part receptacle. A through-groove is formed on a front portion of the power receiving part receptacle. The first engagement portion 112 of the power receiving part 111 may pass through the through-groove and be exposed externally. A front cover 114 is disposed on the front side of the connector 110 facing the power receiving part 111, and a slot 115 is formed on one side of the front cover 114. The first engagement portion 112 may pass through the through-groove and the slot 115 in turn and may be exposed externally of the connector 110.

When a user engages the connector 110 of the endoscope 100 with the connector receptacle 210 of the power providing device 200, the first engagement portion 112 of the connector 110 and the second engagement portion 320 of the power providing device 200 may be engaged with each other with corresponding shapes.

In some embodiments, the first engagement portion 112 may include a first protrusion or a first recess, and the second engagement portion 320 may include a second recess 321 corresponding to the first protrusion or a second protrusion corresponding to the first recess. In this case, the first protrusion of the first engagement portion 112 and the second recess 321 of the second engagement portion 320 may be with each other with corresponding shapes.

When the connector 110 of the endoscope 100 is coupled to the power providing device 200, the slider 300 of the power providing device 200 and the power receiving part 111 are coupled and ready for power to be transferred from the power providing device 200 to the connector 110.

According to embodiments, the slider 300 may provide power to the medical device in a vertical linear motion. The mechanical methods for transmitting power from the power providing device 200 to the endoscope 100 may include a variety of methods, but in this embodiment, the configuration may have a slider-like configuration such that the slider 300 is engaged with the rail structure formed on the power providing device 200 and travels on the rail structure, and much like the slider 300, the power receiving part 111 is engaged with the rail structure formed on the connector 110 and travels on the rail structure.

In such a configuration, movement of the slider 300, powered by the power source 410, may cause the power receiving part 111, which is tightly engaged with the slider 300, to move together, providing power from the light source device to the connector 110.

Since the first engagement portion 112 and the second engagement portion 320 are made of a material of sufficient thickness and stiffness, the engagement force is very high. Therefore, power may be transmitted without loss. Therefore, when the configuration of the slider 300 having the second engagement portion 320 provides power as in the present embodiment, and the connector 110 receiving the power also adopts the configuration of the power receiving part 111 having the first engagement portion 112, the power may be provided accurately and precisely, and problems such as delayed response, uneven response, etc. due to backlash during power transmission may be eliminated.

When the first engagement portion 112 is a protrusion and the second engagement portion 320 is a recess, the edge of the protrusion or recess 321 may be rounded or chamfered. By rounding or chamfering the edges of the protrusion or recess 321, during mutual engagement, the first engagement portion 112 and the second engagement portion 320 may be smoothly engaged and vibration noise may be suppressed.

According to embodiments, the medical device may have a bendable section that is inserted into the subject's body to perform a bending motion in order to collect image information inside the subject's body, wherein the range of motion of the slider 300 may be set to correspond to the range of bending angles of the bendable section.

In the connector 110, the power receiving part 111 is connected to a power transmission part, which is connected to the bendable section via the universal cord, the control body, and the insertion tube.

Therefore, when the power receiving part 111 receives and transmits power to the power transmission part while performing a vertical linear reciprocating motion in the connector 110, the power transmission part transmits power through the universal cord, the control body, and the insertion tube to the bendable section in the connector 110, and the bendable section receiving the power performs a bending motion.

According to embodiments, the power providing device may include a control command receiver 250 receiving a control command signal for controlling a travel distance D of the slider 300 from a medical device; and a power source controller controlling power generation of the power source 410 based on the control command signal received by the control command receiver 250. Here, the control command receiver 250 may also receive an image signal according to an embodiment.

The bendable section performs a vertical bending operation and a horizontal bending operation, and the combination of these operations enables realization of a bending operation in all directions. In order to realize this combination of operations, all of the aforementioned configurations, including the power source 410, the slider 300, the slider receptacle 450, and the slider support 400, may be configured in pairs according to this embodiment.

The control command signal may be generated by the controller disposed in the control body, and the control command signal generated in the control body may be transmitted to the power source controller through the universal cord and a control signal terminal disposed in the connector 110, and through the control command receiver 250 disposed in the connector receptacle 210 of the power providing device 200. When a user couples the connector 110 to the connector receptacle 210 in order to transmit the control signal, the control signal terminal of the connector 110 and the control command receiver 250 disposed in the connector receptacle 210 in a position in the connector receptacle 210 corresponding to the position in which the control signal terminal of the connector 110 is disposed are electrically coupled. Thus, an electrical control signal may be transmitted. The control command signals may include control commands to control vertical bending and horizontal bending of the bendable section, and the power source controller may receive the control commands to control the power source 410 to provide power. One of the pair of sliders 300 may provide power to realize vertical bending of the bendable section, and the other of the pair of sliders 300 may provide power to realize horizontal bending of the bendable section.

The pair of power receiving parts disposed in the connector 110 to correspond to the pair of sliders 300 may function similarly.

The power providing device 200 of the present embodiment may include, for example, a light source device providing light in combination with the endoscope 100, or an image processing device receiving and processing image information from the endoscope 100 and transmitting the image to a monitor so that a user may view the image.

The light source device having a light source 260 therein or the image processing device capable of processing the image may be equipped with a power source 410, a power source 410 controller, and power transmission part 330, 412 that transmit power generated by the power source 410 to the slider. That is, a power-providing system capable of providing power to the light source device or the image processing device may be provided.

Hereinafter, the power providing device 200 according to the present embodiment will be denoted as a light source device.

The light source device according to this embodiment may include or more among: a housing 240; a light source 260 disposed inside the housing 240 and configured to generate light; an air pump 270 configured to pump air; a power providing part; and one the power providing system.

In accordance with embodiments, in the light source device, a pair of slider supports 400 may be disposed facing each other with an adjustment spacing offered therebetween. Between the pair of slider supports 400 may be disposed a light providing portion 280 and an air-providing portion. The light providing portion 280 may be disposed adjacent to the light source 260 to serve to provide light generated by the light source 260 to the outside. In the endoscope 100, a light guide cable extends from the connector to the tube tip through the universal cord, the control body, and insertion tube.

This structure allows light generated by the light source 260 to be transmitted to the illumination means of the tube tip. A light receiving part 116 and an air receiving part may be disposed in the center of the connector 110, and when a user couples the connector 110 to the connector receptacle 210, the light receiving part 116 and the air receiving part are respectively engaged with the light providing portion 280 and the air providing part, being ready to receive light and air.

Here, the light providing portion 280 and the air providing part may be mounted on a center support, which may be disposed between the two slider supports 400. In this structure, an optical path is arranged for light and air to be transmitted to the center through the connector receptacle 210 and the connector 110, and a pair of second engagement portions 320 for providing power are arranged on both sides of the optical path for transmitting light and air. This structure has advantages, such as being able to increase space efficiency, in a light source device that may transmit power and light simultaneously.

In the specification (particularly, in claims) of the present disclosure, the use of the term "above" and similar denoting terms may correspond to both singular and plural forms. Furthermore, recitation of ranges of values herein are merely intended to refer to respective separate values falling within the respective ranges and, unless otherwise indicated herein, the respective separate values are incorporated herein as if individually recited herein.

The operations of any method described herein may be performed in any suitable order unless otherwise indicated herein or otherwise clearly contradicted by the context. However, the operations shall not be limited to the described sequence. The use of any examples or exemplary languages (e.g., "such as") provided herein is intended merely to better illustrate the present disclosure and does not pose a limitation on the scope of the present disclosure unless otherwise defined by the Claims. In addition, a person having ordinary knowledge in the art will appreciate that various modifications, combinations, and changes are possible according to design conditions and factors within the scope of the claims or equivalents thereof.

Therefore, the spirit of the present disclosure shall not be limited to the above-described embodiments, and the entire scope of the appended claims and equivalents thereof will fall within the scope and spirit of the present disclosure.

DESCRIPTION OF REFERENCE NUMERALS OF DRAWINGS

100: endoscope 110: connector
111: power receiving part
112: first engagement portion
113: base portion 114: front cover
115: slot 120: universal cord
130: control body 131: controller
140: insertion tube 141: bendable section
200: slider 210: connector receptacle
220: through-slot 230: control panel
240: housing
250: control command receiver
260: light source 270: air pump
280: light providing portion
300: slider
310: body portion
320: second engagement portion
321: recess 330: rack gear
340: rail structure (slider engagement portion)
400: slider support
410: power source 411: driving shaft
412: pinion gear
420: location information collecting part
430: bottom fastener 440: body portion
441: driving shaft through-hole
450: slider receptacle
451: rail sidewall 500: lid cover

The invention claimed is:

1. A medical device comprising:
an endoscope comprising a connector;
a power providing device comprising a connector receptacle on a front portion of the power providing device and coupled to the connector, a power source configured to generate power, a power transmission part configured to transmit power generated by the power source, and a slider configured to operate by receiving power from the power transmission part and provide the power to the endoscope; and
a slider support supporting the slider and having a slider engagement portion operably engaging the slider,
wherein the connector comprises a first engagement portion configured to receive power,
the slider has a second engagement portion configured to interact with the first engagement portion to provide power to the first engagement portion,
the slider provides power to the endoscope by performing a vertical linear motion,
the second engagement portion protrudes in a direction of the front portion different from a direction of the vertical linear motion of the slider, and,
the second engagement portion of the slider is configured to move vertically and linearly by receiving power generated by the power source, the first engagement portion engaged with the second engagement portion is configured to move together with the second engagement portion to provide power to the connector.

2. The medical device of claim 1, wherein the slider engagement portion comprises a rail engagement structure provided on the slider support and the slider to allow the slider to move linearly along the slider support.

3. The medical device of claim 1, wherein the first engagement portion has a first protrusion or a first recess, and the second engagement portion has a second recess, corresponding to the first protrusion, or the second engagement portion has a second protrusion, corresponding to the first recess.

4. The medical device of claim 1, wherein the power transmission part comprises:
a pinion gear connected to a driving shaft of the power source; and
a rack gear formed on one side of the slider and engaged with the pinion gear.

5. The medical device of claim 1, wherein the slider support is provided with a slider receptacle formed to surround, receive, and engage the slider with a rail structure.

6. The medical device of claim 1, wherein the endoscope further comprises a bendable section configured to be inserted into the subject's body and perform a bending motion in order to collect image information of the interior of the subject's body, wherein the motion of the slider has a range corresponding to a range of bending angles of the bendable section.

7. The medical device of claim 1, wherein the power providing device comprises:
a control command receiver configured to receive a control command signal controlling a travel distance of the slider from the endoscope; and
a power source controller configured to control power generation of the power source on the basis of the control command signal received by the control command receiver.

* * * * *